United States Patent
Lazarof (10) Patent No.: US 10,092,473 B2
(45) Date of Patent: *Oct. 9, 2018

(54) DENTAL CHAIR

(71) Applicant: Bio-Dent, Inc., Encino, CA (US)

(72) Inventor: Sargon Lazarof, Encino, CA (US)

(73) Assignee: Bio-Dent, Inc., Encino, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/272,126

(22) Filed: Sep. 21, 2016

(65) Prior Publication Data
US 2017/0071811 A1    Mar. 16, 2017

Related U.S. Application Data

(63) Continuation of application No. 14/640,966, filed on Mar. 6, 2015, now Pat. No. 9,456,948.

(51) Int. Cl.
| | |
|---|---|
| A47C 7/62 | (2006.01) |
| A47B 83/02 | (2006.01) |
| F16L 3/22 | (2006.01) |
| A47F 7/00 | (2006.01) |
| A61G 15/10 | (2006.01) |
| A61G 15/18 | (2006.01) |
| A61G 15/02 | (2006.01) |
| A61C 17/02 | (2006.01) |
| A61C 17/16 | (2006.01) |
| A61G 15/12 | (2006.01) |
| A61G 12/00 | (2006.01) |

(52) U.S. Cl.
CPC .......... *A61G 15/10* (2013.01); *A61C 17/0214* (2013.01); *A61C 17/16* (2013.01); *A61G 15/02* (2013.01); *A61G 15/12* (2013.01); *A61G 15/18* (2013.01); *A61G 12/002* (2013.01)

(58) Field of Classification Search
CPC ........ A61G 15/02; A61G 15/10; A61G 15/12; A61G 15/18; A61G 12/002; A61C 17/0214; A61C 17/16
USPC ....... 297/135, 144, 145, 146, 147, 160, 161, 297/162, 188.04, 188.05, 188.06, 188.07, 297/330, 188.01; 248/68.1; 211/68, 69
See application file for complete search history.

(56) References Cited

U.S. PATENT DOCUMENTS

| | | |
|---|---|---|
| 3,129,033 A | 4/1964 | Emmerson |
| 3,198,574 A | 8/1965 | Ota et al. |
| 3,222,105 A | 12/1965 | Cross |
| 3,311,411 A | 3/1967 | Page |
| 3,386,766 A | 6/1968 | Gorelick |
| 3,415,571 A | 12/1968 | Heimert, III |
| 3,429,516 A * | 2/1969 | Sharp .............. A61G 15/16 242/388.9 |
| 3,445,934 A | 5/1969 | Harris |
| 3,524,676 A | 8/1970 | Cocherell et al. |
| 3,530,513 A | 9/1970 | Maurer et al. |
| 3,556,669 A | 1/1971 | Valeska et al. |
| 3,640,552 A | 2/1972 | Demler, Sr. et al. |
| 3,650,033 A | 3/1972 | Behne et al. |

(Continued)

*Primary Examiner* — Rodney Barnett White
(74) *Attorney, Agent, or Firm* — Mintz Levin Cohn Ferris Glovsky and Popeo, P.C.

(57) ABSTRACT

A dental chair is provided including a chair assembly comprising a backrest, a seat, and a base; and at least one set of utility ports disposed on the chair, adjacent to the seat, each port having a quick release fitting for receiving a flexible conduit connected to a hand piece.

15 Claims, 9 Drawing Sheets

(56) References Cited

U.S. PATENT DOCUMENTS

| | | | |
|---|---|---|---|
| 3,653,125 A | 4/1972 | Heubeck | |
| 3,662,465 A | 5/1972 | Heubeck | |
| 3,693,258 A * | 9/1972 | Fulton | A61G 15/16 433/78 |
| 3,755,899 A | 9/1973 | Betush | |
| 3,757,421 A | 9/1973 | Kraft | |
| 3,771,226 A | 11/1973 | Lieb et al. | |
| 3,778,903 A | 12/1973 | Gardella et al. | |
| 3,790,971 A | 2/1974 | Fox | |
| 3,823,475 A | 7/1974 | Heubeck | |
| 3,895,764 A * | 7/1975 | Roland | A61G 15/16 242/378.2 |
| 3,972,120 A | 8/1976 | Cope | |
| 3,986,263 A | 10/1976 | Borgelt et al. | |
| 4,069,587 A | 1/1978 | Peralta | |
| 4,080,737 A | 3/1978 | Fleer | |
| 4,114,273 A * | 9/1978 | McGaha | A61G 15/16 242/385.1 |
| 4,114,274 A | 9/1978 | Jones | |
| 4,145,813 A | 3/1979 | Hall | |
| 4,151,648 A * | 5/1979 | Hirth | A61G 15/16 137/355.19 |
| 4,209,907 A | 7/1980 | Tsukada et al. | |
| 4,226,590 A | 10/1980 | Hofmann | |
| 4,249,900 A | 2/1981 | Hoelzer et al. | |
| 4,260,376 A | 4/1981 | Litel et al. | |
| 4,286,948 A | 9/1981 | Pietschmann | |
| 4,311,461 A | 1/1982 | Hotta et al. | |
| 4,332,555 A | 6/1982 | Richardson | |
| 4,427,382 A | 1/1984 | Hoffmeister et al. | |
| 4,470,811 A * | 9/1984 | Heubeck | A61G 15/16 433/108 |
| 4,500,134 A | 2/1985 | Kaneko et al. | |
| 4,514,172 A | 4/1985 | Behringer | |
| 4,516,805 A | 5/1985 | Leeper et al. | |
| 4,527,976 A | 7/1985 | Behringer et al. | |
| 4,610,630 A | 9/1986 | Betush | |
| 4,630,862 A | 12/1986 | Watanabe | |
| 4,883,316 A | 11/1989 | Austin, Jr. et al. | |
| 4,900,065 A | 2/1990 | Houck | |
| 5,107,899 A | 4/1992 | Murphy | |
| 5,176,423 A | 1/1993 | Austin, Jr. et al. | |
| 5,342,097 A | 8/1994 | Hanson | |
| 5,348,472 A | 9/1994 | Joeckel et al. | |
| 5,450,874 A * | 9/1995 | Hamula | A61G 15/18 137/355.23 |
| 5,480,212 A | 1/1996 | Marconet | |
| 5,873,717 A | 2/1999 | Behringer | |
| 5,884,350 A | 3/1999 | Kurze | |
| 6,406,294 B1 | 6/2002 | Bell | |
| 6,484,959 B1 * | 11/2002 | Grammenz | A61G 15/18 137/355.2 |
| 6,591,239 B1 | 7/2003 | McCall et al. | |
| 6,626,496 B2 | 9/2003 | Beach et al. | |
| 6,793,490 B2 | 9/2004 | Bianchetti et al. | |
| 6,916,065 B2 | 7/2005 | Park | |
| 7,195,219 B2 | 3/2007 | Irwin et al. | |
| 7,211,034 B2 | 5/2007 | Beard | |
| 7,347,492 B2 | 3/2008 | DiRe | |
| 8,408,899 B1 | 4/2013 | Smith et al. | |
| 8,770,971 B2 | 7/2014 | Boren | |
| 9,456,948 B1 | 10/2016 | Lazarof | |
| 2004/0059197 A1 | 3/2004 | Yamashita et al. | |
| 2008/0122269 A1 | 5/2008 | Tatlock | |
| 2011/0059416 A1 | 3/2011 | Lee | |
| 2011/0195374 A1 * | 8/2011 | Boren | A61G 15/002 433/33 |
| 2013/0118503 A1 * | 5/2013 | Galatas | A61G 15/14 128/845 |

* cited by examiner

DENTAL CHAIR

CROSS REFERENCE TO RELATED APPLICATIONS

This application is a continuation of U.S. application Ser. No. 14/640,966, filed on Mar. 6, 2015, and entitled "Dental Chair," now U.S. Pat. No. 9,456,948, the disclosure of which is incorporated herein by reference for all purposes.

BACKGROUND OF THE INVENTION

This invention is related to the field of dentistry. More specifically this invention is related to the field of dental chairs.

Dentists and hygienists need electricity, compressed air, vacuum, and water available at the dental chair when performing dental procedures. The dental chair is connected to utilities, typically through a junction box that supplies these various requirements, via a compressor, vacuum pump, fresh water plumbing and drain piping to various hand pieces (such as a drill). The junction box may be in a separate equipment room or in the base of the chair. Associated plumbing and controls distribute the compressed air and vacuum to ports in the dental chair and flexible conduits connect the ports to the various hand pieces. The dental chair is connected to these utilities by plumbing with connections either in the floor or an umbilical from the wall or ceiling.

This invention has as its primary object the provision of an attachment for dental chairs for supporting the various hand pieces and associated hardware used by a dentist, hygienist or other operator. The location of the various hand pieces and associated hardware must enable movement by the operator, when needed, and be in a convenient position relative to the mouth of a patient while in a recumbent position in the dental chair, reducing movement of the dentist and/or patient.

For certain individuals, going to a dentist may cause anxiety, nervousness, and or general phobic reactions. It would be desirable to keep the various hand pieces and associated hardware out of view of the patient in an effort to reduce such anxiety and the like.

Examples of various dental chairs and associated hardware include the following:

U.S. Pat. No. 3,129,033 (Emerson) discloses an attachment to a dental chair for supporting various hand pieces. The attachment is located adjacent to a side of the chair for ready accessibility by a dentist.

U.S. Pat. No. 6,406,294 (Bell) discloses a self-contained dental chair with an integrated compressor, vacuum pump, water reservoir, waste container and associated fittings, wiring, and plumbing. The design allows the chair to be relocated without having to connect to facility air, water and waste.

U.S. Patent Pub. No. 2011/0195374 (Boren) discloses a mobile dental chair that includes an adjustable backrest, an adjustable headrest, integrated dental tools. Various utilities are provided in the base of the chair.

All references cited herein are incorporated herein by reference in their entireties.

BRIEF SUMMARY OF THE INVENTION

In an exemplary embodiment of the present invention, a dental chair is provided which includes a chair assembly having a backrest, a seat, and a base. At least one set of utility ports is disposed on the chair on or adjacent to the seat. Each port has a quick release fitting for receiving a flexible conduit connected to a hand piece.

The set or sets of utility ports may include a water port for providing water for a water nozzle hand piece, a vacuum port for providing suction to a suction hand piece, a compressed air port for providing compressed air for an air hand piece, and an electricity port for providing electricity for an electric hand piece. The set or sets of utility ports may each include utility ports that are disposed adjacent to one another. Each set of utility ports may be disposed on the chair wherein at a different location on the chair. One set of utility ports of the at least one set of utility ports may be located on the base of the chair adjacent the seat on the left side of the chair and another set of the at least one set of utility ports may be located on the base of the chair adjacent the seat on the right side of the chair.

In another exemplary embodiment of the present invention, a dental chair is provided including a chair assembly having a backrest, a seat, and a base. The backrest has a front side and rear side. The rear side has a compartment accessible by an operator while a patient is seated in said chair. A hand piece attachment bracket for receiving the hand pieces is disposed in the compartment. Each of the hand pieces is connected by a flexible conduit to one of a plurality of utilities, such as electricity, water, vacuum, compressed air, drains and the like.

The hand pieces may be, for example, electric driven hand pieces, air driven hand pieces, water, air and suction. One or more retractors may be provided to retract the flexible conduit for each of the hand pieces. The compartment may have a door that moves from an opened position to a closed position, wherein when the door is in the closed position, the hand piece attachment bracket and the hand pieces are not visible to the operator and patient. When the door is in the opened position, the operator has access to the hand pieces. A slide-out tray may be disposed in the base that slides from a concealed position in the base to an accessible position for use by the operator. Each flexible conduit may be releasably attachable by a quick release fitting to one of several utility ports disposed on the base adjacent to the seat. Each utility port may be disposed on one side or both sides of the base adjacent to a side of the operator such that the operator may select which side of the base to attach each flexible conduit. Alternatively, or additionally, each utility port may be disposed adjacent to the rear side of the backrest of the chair.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The invention will be illustrated in more detail with reference to the following embodiments, but it should be understood that the present invention is not deemed to be limited thereto.

Referring now to the drawing figures, wherein like reference numbers refer to like elements throughout the several views, there is shown in FIGS. 1 and 2-4 a dental chair 10 in accordance with one exemplary embodiment of the present invention. The dental chair 10 may include various features common on dental chairs, including, for example, a chair assembly 12 having a seat 14 and a backrest 16, and a base 18. A mechanism 20 on the base 18 elevates the chair assembly 12, and another mechanism 22 reclines the backrest 16. The dental chair 10 may also include armrests 24, a headrest 26, and other features common on dental chairs. Additionally, the dental chair 10 may include speakers 28 in the headrest 26 (for example, on pivoting flaps), connectable to an audio source by, for example, a Bluetooth wireless connection. A viewable display screen 30 (for display of movies, videos, or the like) may be attached to the backrest 16 or headrest 26, by, for example, a pivoting linkage 32 that is adjustable for easy viewing by the patient. An eye shield may protect the patient's eyes.

In an exemplary embodiment, the dental chair 10 includes one or more sets 34 of utility ports 34a, 34b, 34c, 34d disposed on the chair 10, each set located at a position adjacent to the seat 14. Each port 34a, 34b, 34c, 34d, 34e, each having a quick release fitting 36a, 36b, 36c, 36d (see FIG. 1A) for receiving a flexible conduit 38a, 38b, 38c, 38d connected to a hand piece, 40a, 40b, 40c, 40d, 40e.

Figure 1:
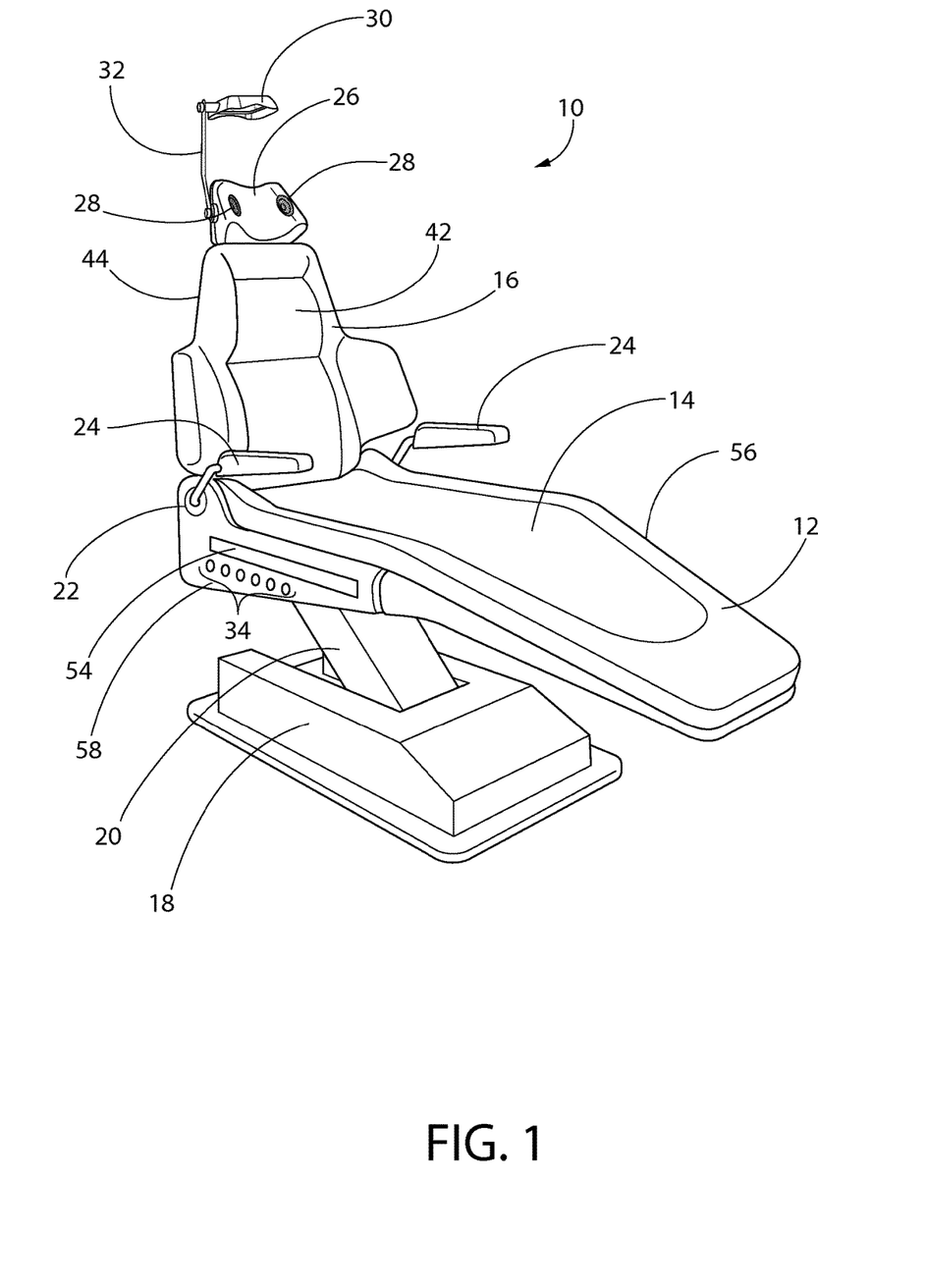
FIG. 1 is a front, isometric view of a dental chair in accordance with a first exemplary embodiment of the present invention.
Figure 1A:
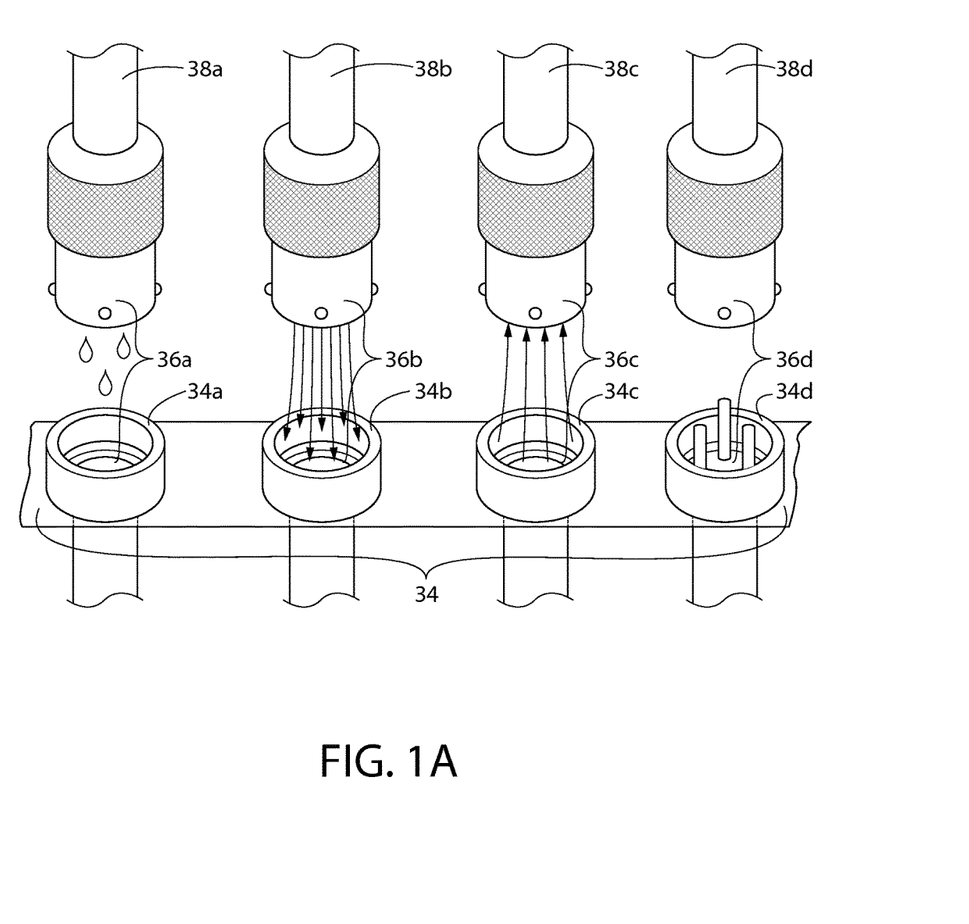
FIG. 1A is an isometric view of a set of utility ports disposed on the dental chair of FIG. 1.
Figure 2:
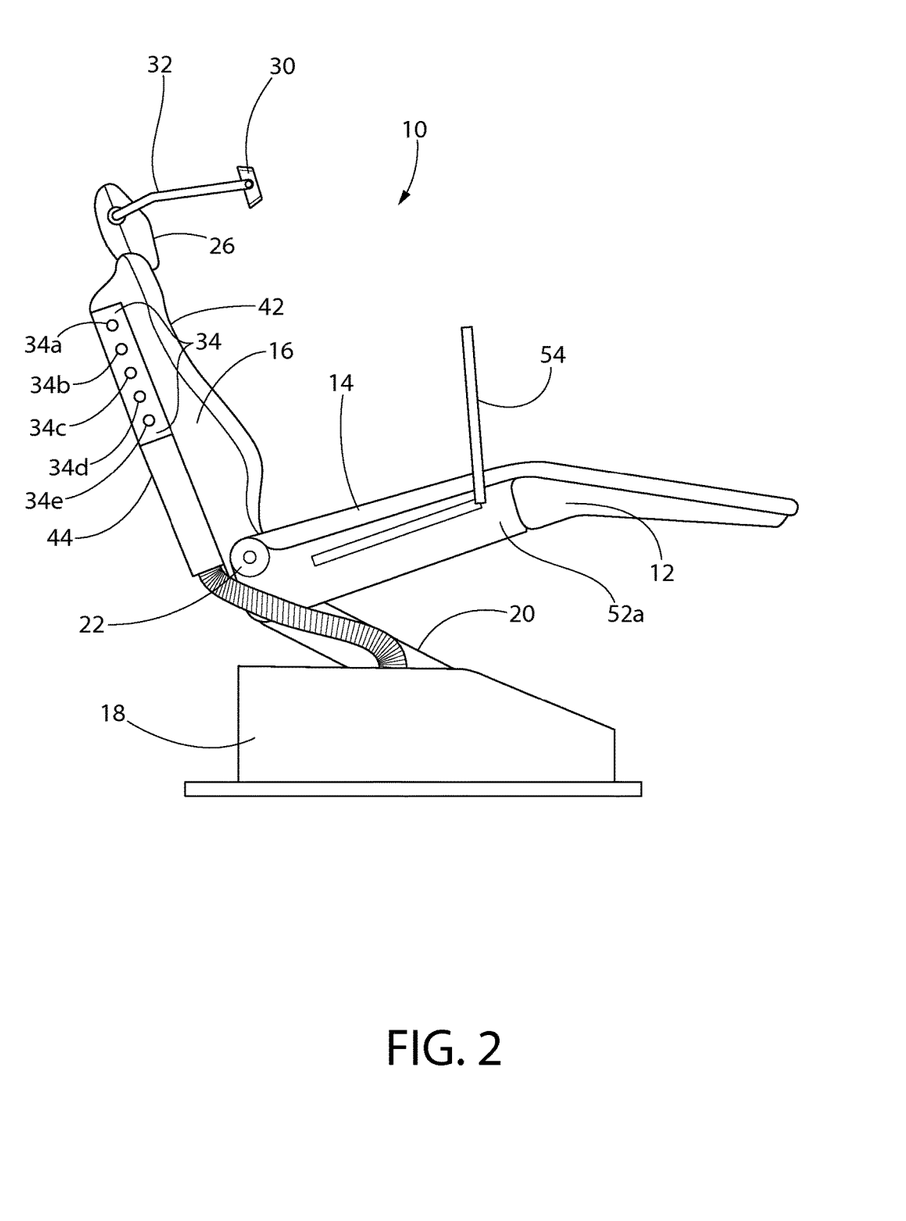
FIG. 2 is a side elevation view of the dental chair of FIG. 1, shown with the set of utility ports adjacent to the backrest of the chair and with a slide-out tray in an extended position.

As seen in the example of FIG. 1A, the sets 34 of utility ports may include one or more of a water port 34a for providing water for a water nozzle hand piece 40a, a vacuum port 34b for providing suction to a suction hand piece 40b, a compressed air port 34c for providing compressed air for an air hand piece 40c, and an electricity port 34d for providing electricity for an electric hand piece 40d.

Each set 34 of utility ports 34a, 34b, 34c, 34d has ports that are preferably disposed adjacent to one another. However, alternatively, the ports in a set 34 may be located at different positions on the chair 10 and need not be adjacent to one another.

If there are multiple sets 34 of utility ports, each set is preferably located at a different location on the chair 10. For example, a set 34 may be placed on the base 18 of the chair 10 adjacent to the right side 58 of the chair 10 (see, FIGS. 1 and 4), and/or another set 34 may be placed on the base 18 of the chair adjacent to the left side 56 of the chair 10 (not shown, but similar to that shown in FIG. 1), and/or another set 34 may be placed on the side of the backrest 16 of the chair 10 (see FIG. 2), and/or another set may be placed on the back of the backrest 16 of the chair 10 (see FIG. 3). It is anticipated that each set 34 may be placed anywhere on the chair where it may function properly.

The sets 34 of utility ports, as described offer numerous advantages over the prior art, including easily sterilizable flexible conduits, and the ability to keep the hand pieces and conduit out of view of the patient until a procedure begins.

Figure 3:
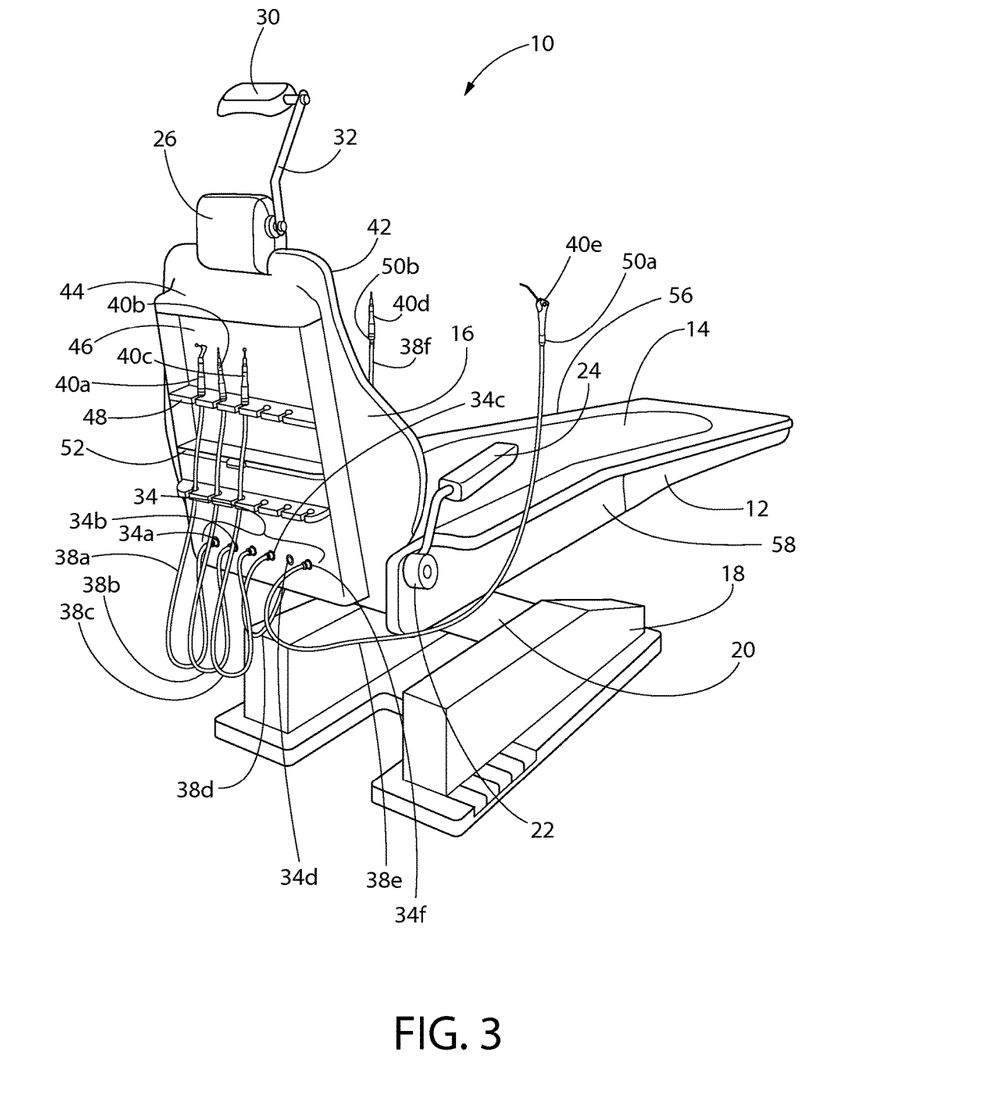
FIG. 3 is a rear isometric view of the dental chair of FIG. 1, shown with the set of utility ports adjacent to the backrest of the chair, and shown with dental hand pieces disposed on a horizontal hand piece attachment bracket on the rear of the backrest of the chair.
Figure 4:
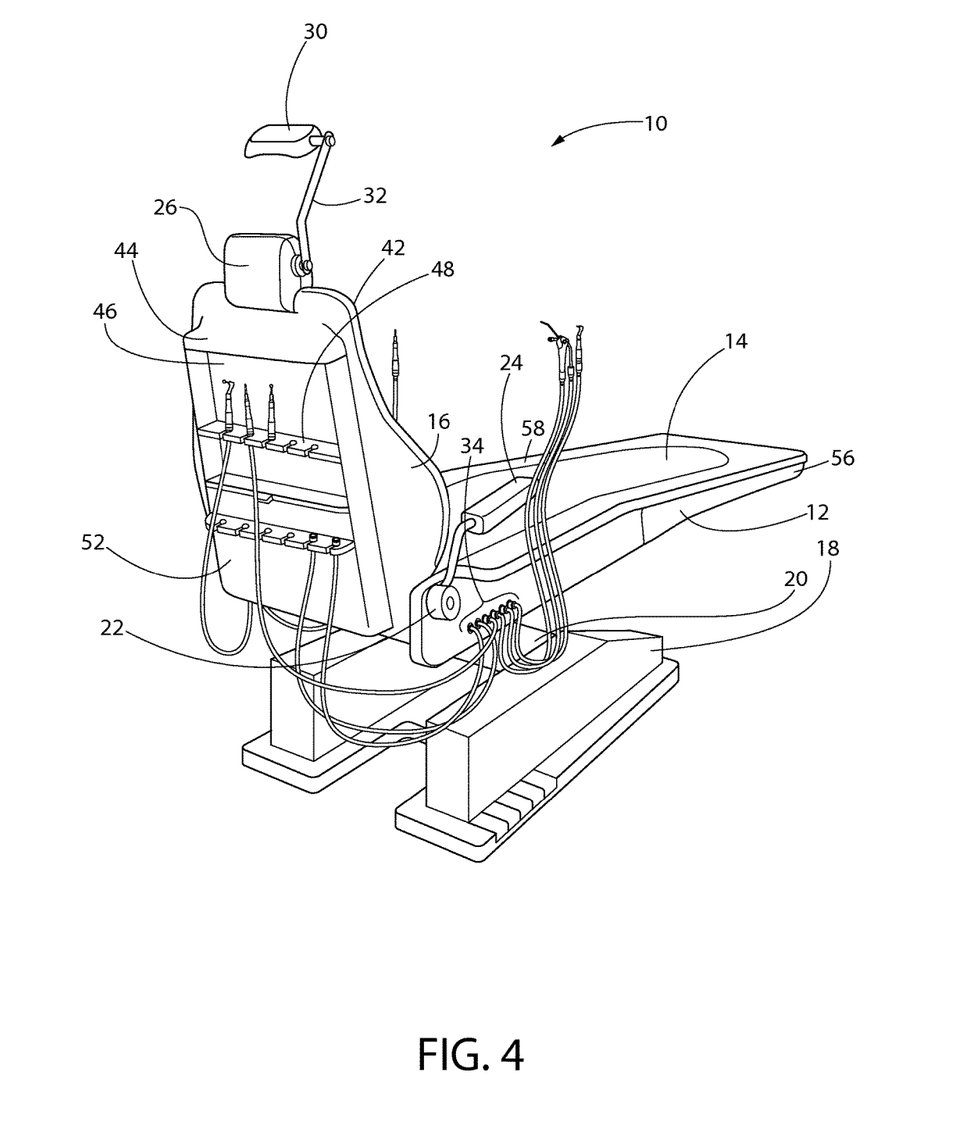
FIG. 4 is a rear, isometric of the dental chair of FIG. 1, shown with the set of utility ports on the frame of the chair adjacent to the seat of the chair.
Figure 5:
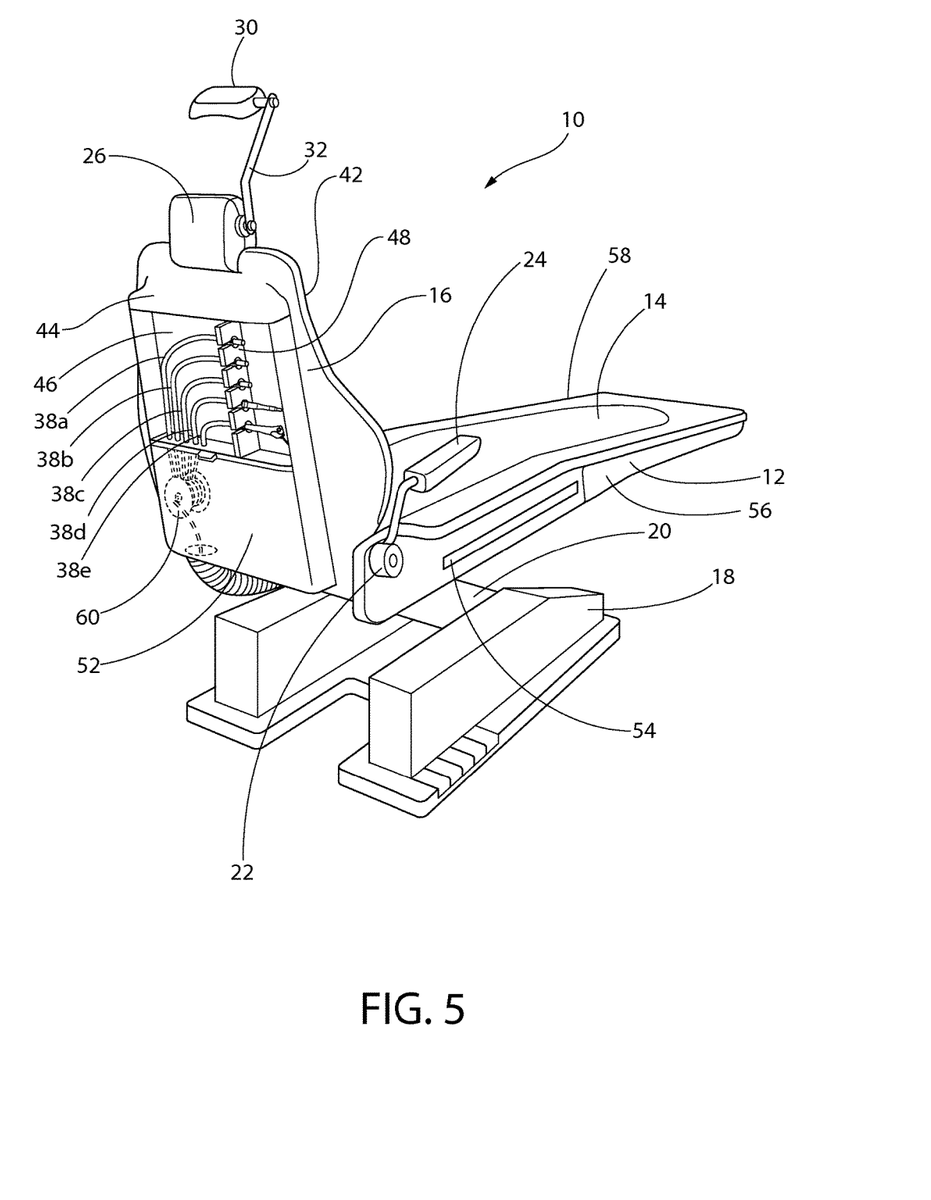
FIG. 5 is a rear, isometric view of a dental chair in accordance with another exemplary embodiment of the present invention, shown with dental hand pieces disposed on a vertical hand piece attachment bracket and with associated flexible conduits in retracted positions using a retractor.

The backrest 16 has a front side 43 and rear side 44. Both the backrest 16 and the seat 14 are preferably cushioned. In accordance with another exemplary embodiment of the present invention as shown in FIGS. 3-8, the rear side 44 of the backrest 16 has a compartment 46 accessible by an operator (e.g., a dentist, hygienist, or the like) while a patient is seated in the chair 10. A hand piece attachment bracket 40 for receiving a plurality of hand pieces 40a, 40b, 40c, 40d, 40e is disposed in the compartment 46 (for example, either horizontally oriented as shown in FIG. 3 or vertically oriented as shown in FIG. 5). Each of the hand pieces 40a, 40b, 40c, 40d, 40e is connected by a flexible conduit 38a, 38b, 38c, 38d, 38e to one the ports 34a, 34b, 34c, 34d of the set 34 of utility ports.

The hand pieces 40a, 40b, 40c, 40d, 40e may be those commonly seen associated with dental chairs such as electric driven hand pieces (dental drills and like), air driven hand pieces, water, air and suction.

Figure 6:
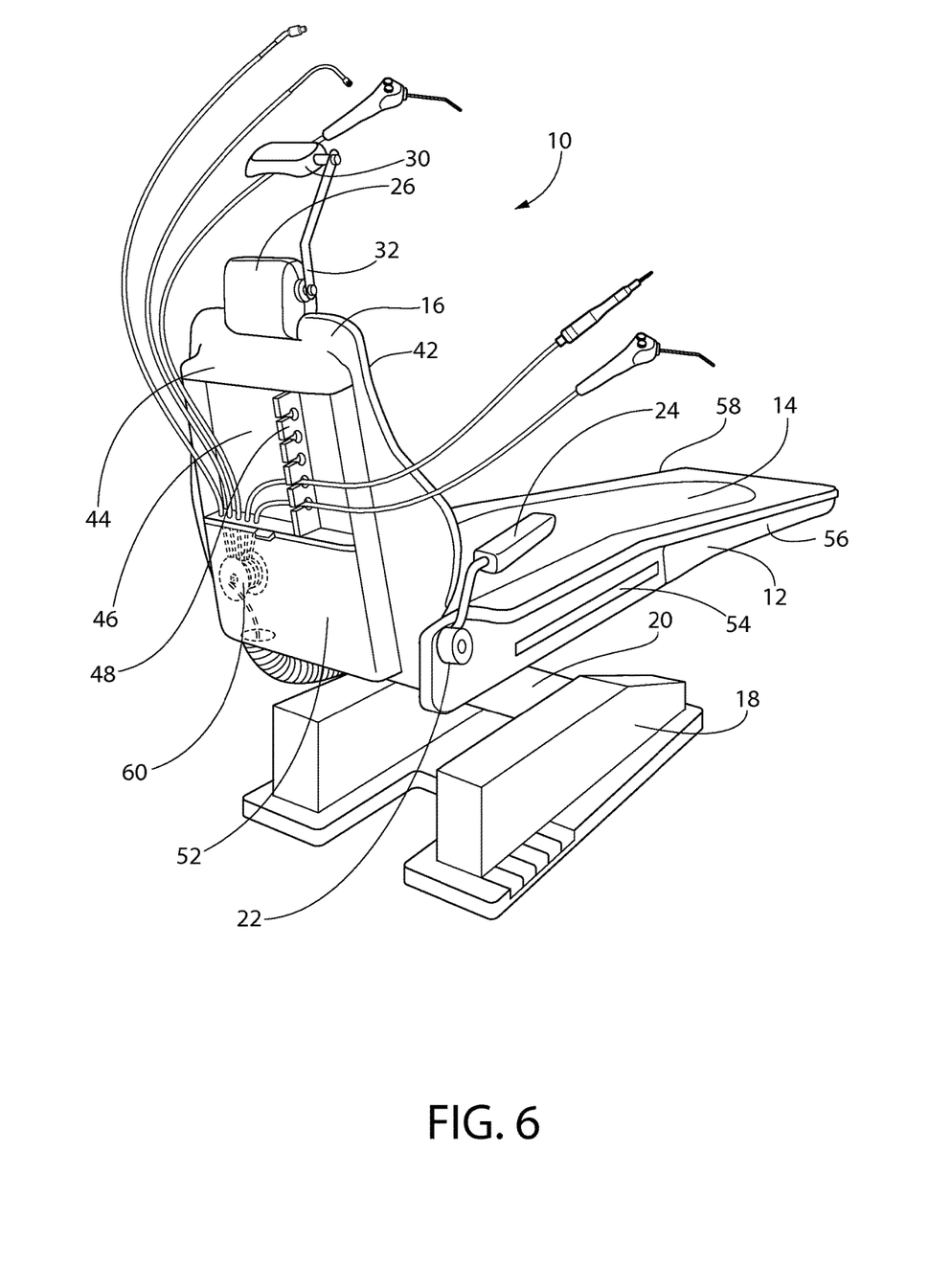
FIG. 6 is a rear, isometric view of the dental chair of FIG. 5, shown with flexible conduits for hand pieces in extended positions.
Figure 7:
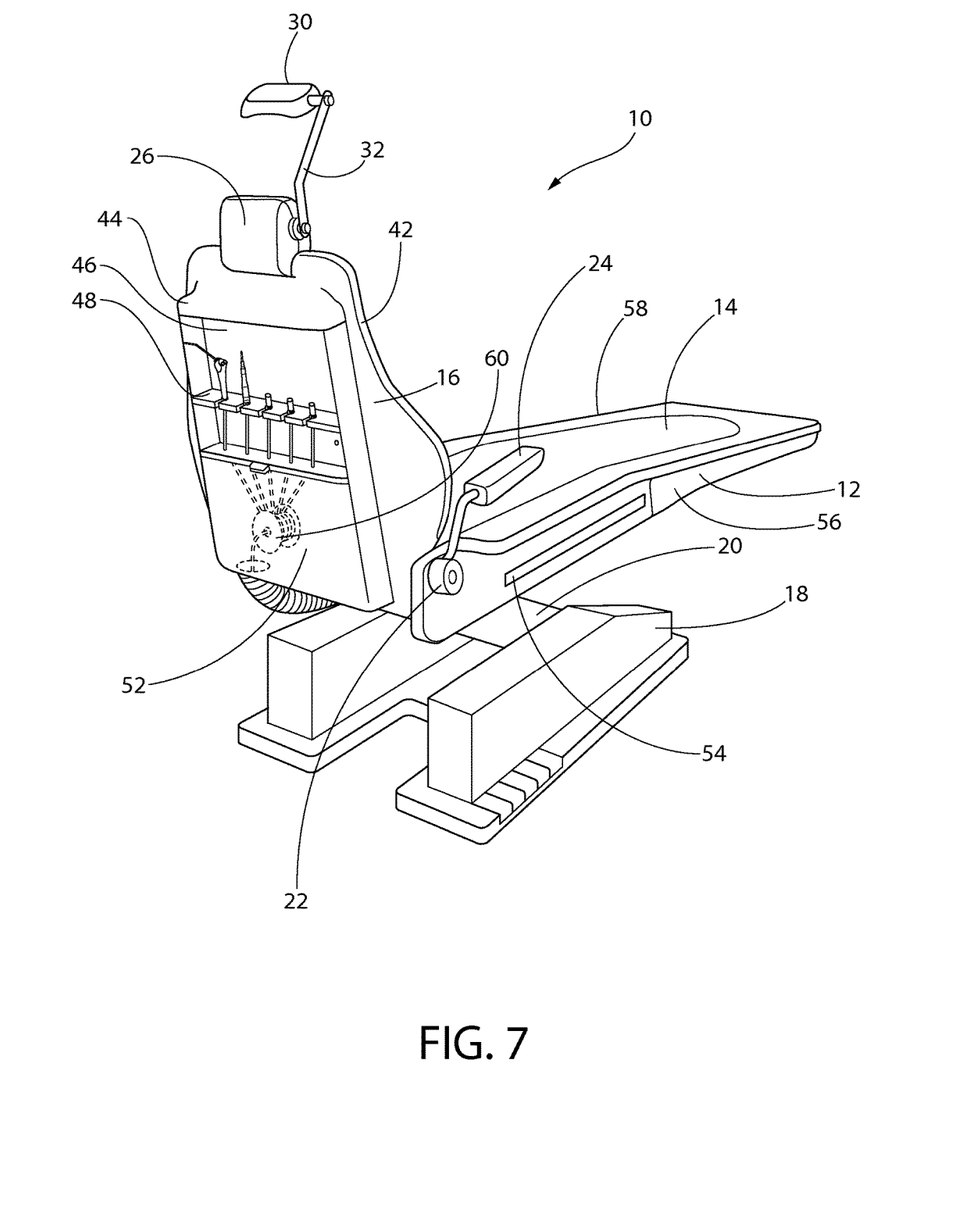
FIG. 7 is a rear, isometric view of the dental chair of FIG. 5, shown with flexible conduits for hand pieces in retracted positions and mounted on a horizontal hand piece attachment bracket.
Figure 8:
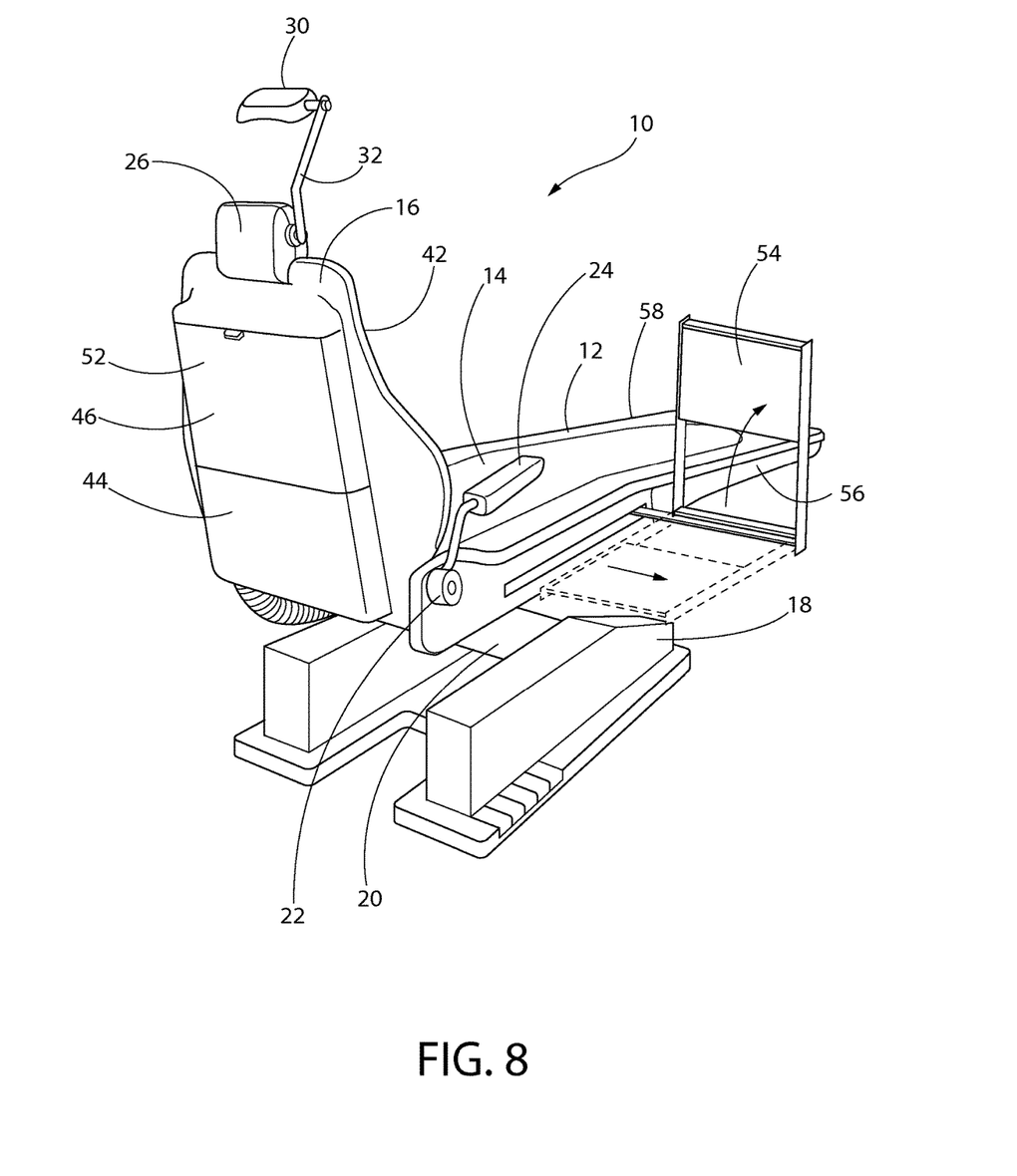
FIG. 8 is a rear, isometric view of the dental chair of FIG. 5, shown with a door for hiding the hand pieces and conduits in a compartment on the rear of the chair.

As best seen in FIGS. 5-7, a retractor 60 for each hand piece 40a, 40b, 40c, 40d, 40e may be included that allows for the retraction of the flexible conduits 38a, 38b, 38c, 38d for each of the plurality of hand pieces 40a, 40b, 40c, 40d, 40e, to keep the various hand pieces and associated hardware neat and organized. This retraction may be accomplished for all flexible conduits 38a, 38b, 38c, 38d simultaneously, or for each flexible conduit independently.

Each flexible conduit 38a, 38b, 38c, 38d may be releasably attachable by a quick release fitting 50a, 50b (see FIG. 3) to a hand piece 40a, 40b, 40c, 40d, 40e at one end of each flexible conduit.

The compartment 46 of the dental chair 10 may have a door 52 that moves from an opened position (see, for example, FIGS. 3-7) to a closed position (see FIG. 8), wherein when the door 52 is in the closed position, the hand piece attachment bracket 48 and plurality of hand pieces 40a, 40b, 40c, 40d, 40e are not visible to the operator and the patient. When the door 52 is in the opened position, the operator has access to any of the hand pieces 40a, 40b, 40c, 40d, 40e.

A slide-out tray 54 may disposed in the base 18 that is slidable from a concealed position in the base 18 (see FIGS. 1 and 5-7) to an accessible position (see FIG. 2) for use by the operator.

While numerous variations of utility port set 34 configurations are shown and described in the present specification, it is not intended to be limiting in any respect. Each set of utility ports 34 can have any reasonable number of ports of the same or different types that are compatible with various flexible conduits 38 and hand pieces 40.

While the invention has been described in detail and with reference to specific embodiments thereof, it will be apparent to one skilled in the art that various changes and modifications can be made therein without departing from the spirit and scope thereof.

What is claimed is:

1. A dental chair comprising:
   (a) a chair assembly comprising a backrest, a seat, and a base; and
   (b) a plurality of sets of utility ports comprising a first set of utility ports and a second set of utility ports, each port, of the first set of utility ports and/or the second set of utility ports, having a quick release fitting for receiving a flexible conduit connected to a hand piece, the first set of utility ports being disposed on one side of the seat of the chair assembly, and the second set of utility ports being disposed on a different side of the seat of the chair assembly than the first set of utility ports.

2. The dental chair of claim 1, wherein at least one set of utility ports of the plurality of sets of utility ports comprises a water port for providing water for a water nozzle hand piece, a vacuum port for providing suction to a suction hand piece, a compressed air port for providing compressed air for an air hand piece, and an electricity port for providing electricity for an electric hand piece.

3. The dental chair of claim 1, wherein at least one set of utility ports of the plurality of sets of utility ports includes utility ports that are disposed adjacent to one another.

4. The dental chair of claim 1, wherein the plurality of sets of utility ports includes a third set of utility ports disposed at a different location on the chair assembly than the first set of utility ports and/or the second set of utility ports.

5. The dental chair of claim 4, wherein the first set of utility ports is disposed on the a left side of the seat of the chair assembly, and wherein the second set of utility ports is disposed on a right side of the seat of the chair assembly.

6. A dental chair, comprising:
   (a) a chair assembly comprising a backrest, a seat, and a base, the backrest having a front side and a rear side, the rear side of the backrest having a compartment with a hand piece attachment bracket disposed therein, the hand piece attachment bracket configured to receive one or more hand pieces; and
   (b) a plurality of hand pieces, each of the plurality of hand pieces being coupled with a flexible conduit that is releasably attached to a corresponding utility port from a plurality of utility ports disposed on the chair assembly, at least some of the plurality of hand pieces configured to be received by the hand piece attachment bracket disposed in the compartment in the rear side of the backrest of the chair assembly, the flexible conduit coupled with each of the plurality of hand pieces configured to retract into the backrest of the chair assembly.

7. The dental chair of claim 6, wherein the plurality of hand pieces are hand pieces selected from the group consisting of electric driven hand pieces, air driven hand pieces, water, air and suction.

8. The dental chair of claim 6, further comprising at least one retractor configured to retract one or more of the flexible conduit coupled with each of the plurality of hand pieces.

9. The dental chair of claim 6, wherein the compartment is accessible by an operator while a patient is seated in the dental chair, wherein the compartment has a door that moves from an opened position to a closed position, wherein the hand piece attachment bracket and one or more of the plurality of hand pieces received by the hand piece attachment bracket are concealed when the door is in the closed position, and wherein the one or more of the plurality of hand pieces received by the hand piece attachment bracket are accessible when the door is in the opened position.

10. The dental chair of claim 6, further comprising a slide-out tray disposed in the base of the chair assembly, the slide-out tray being slidable from a concealed position in the base to an accessible position for use by the operator.

11. The dental chair of claim 6, wherein each of the plurality of hand pieces are releasably attachable to the corresponding utility port by a quick release fitting, and wherein the at least some of the plurality of utility ports are disposed on the base of the chair assembly, adjacent to the seat.

12. The dental chair of claim 11, wherein at least some of the plurality of utility ports are disposed on a side of the base adjacent to a side of the operator.

13. The dental chair of claim 11, wherein the plurality of utility ports are disposed on both sides of the base, and wherein the flexible conduit is attachable to a utility port disposed on either side of the base.

14. The dental chair of claim 11, wherein at least some of the plurality of utility ports are disposed adjacent to the rear side of the backrest of the chair.

15. The dental chair of claim 6, wherein the flexible conduits coupled with each of the plurality of hand pieces are configured to retract individually and/or simultaneously into the backrest of the chair assembly.

* * * * *